United States Patent [19]

Shiratsuchi et al.

[11] Patent Number: 4,678,803
[45] Date of Patent: Jul. 7, 1987

[54] OPTICAL ISOMERS, PROCESSES FOR PRODUCTION THEREOF AND PHARMACEUTICAL COMPOSITION THEREOF

[75] Inventors: Masami Shiratsuchi, Musashimurayama; Kiyoshi Kawamura, Tokorozawa; Toshihiro Akashi; Hiroshi Ishihama, both of Higashimurayama; Yasumi Uchida, Ichikawa, all of Japan

[73] Assignee: Kowa Company, Ltd., Nagoya, Japan

[21] Appl. No.: 716,462

[22] Filed: Mar. 27, 1985

[30] Foreign Application Priority Data

Mar. 31, 1984 [JP]  Japan .................................. 59-62177

[51] Int. Cl.$^4$ ...................... A61K 31/35; C07D 311/64
[52] U.S. Cl. ...................................... 514/456; 549/399
[58] Field of Search .......................... 549/399; 514/456

[56] References Cited

U.S. PATENT DOCUMENTS 4,394,382  7/1983  Shiratsuchi et al. ................ 549/399

*Primary Examiner*—Nicky Chan
*Attorney, Agent, or Firm*—Wenderoth, Lind & Ponack

[57] ABSTRACT

An optical isomer selected from the group consisting of (2'R),(3R)-3,4-dihydro-8-(2'-hydroxy-3'-isopropylamino)propoxy-3-nitroxy-2H-1-benzopyran, (2'S),(3R)-3,4-dihydro-8-(2'-hydroxy-3'-isopropylamino)propoxy-3-nitroxy-2H-1-benzopyran and acid addition salts of these isomers, process for producing these isomers and a pharmaceutical composition thereof useful for the treatment of cardiovascular diseases.

3 Claims, No Drawings

OPTICAL ISOMERS, PROCESSES FOR PRODUCTION THEREOF AND PHARMACEUTICAL COMPOSITION THEREOF

This invention relates to novel optical isomers of 3,4-dihydro-8-(2'-hydroxy-3'-isopropylamino)propoxy-3-nitroxy-2H-1-benzopyran (to be sometimes abbreviated K-351 in this invention), acid addition salts thereof, processes for production thereof, and also to a pharmaceutical composition comprising such an isomer or an acid addition salt thereof.

More specifically, this invention relates to an optical isomer selected from the group consisting of (2'R),(3R)-3,4-dihydro-8-(2'-hydroxy-3'-isopropylamino)-propoxy-3-nitroxy-2H-1-benzopyran (to be sometimes abbreviated as R-R.K-351 in this invention) represented by the following formula (A-2), (2'S),(3R)-3,4-dihydro-8-(2'-hydroxy-3'-isopropylamino)propoxy-3-nitroxy-2H-1-benzopyran (to be sometimes abbreviated as S-R.K-351 in this invention) represented by the following formula (B-2)

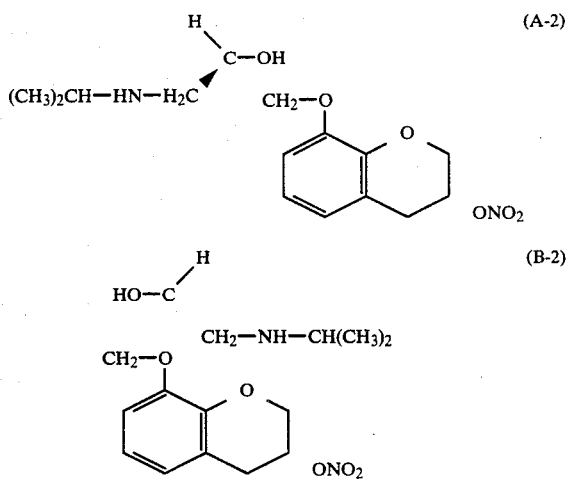

and acid addition salts of these isomers, processes for production thereof, and to pharmaceutical compositions comprising these compounds.

K-351 is a known compound represented by the following formula

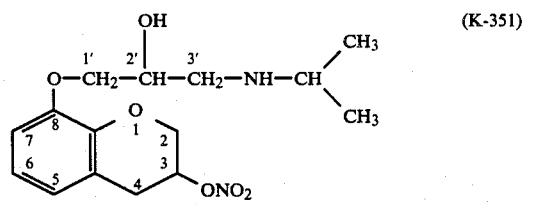

It is useful as a drug for the cardiovascular diseases having beta-blocking activity and vasodilating activity (direct vasodilating activity and alpha-blocking activity) (Japanese Laid-Open Patent Publications Nos. 7481/1982 and 106619/1982, and corresponding U.S. Pat. No. 4,394,382 and European Laid-Open Patent Publication No. 42299).

Since K-351 has asymmetric carbon atoms at the 3-position of the benzopyran ring and the 2'-position of the side chain, two racemates, i.e. 4 optical isomers, can exist theoretically. However, no mention has previously been made on the racemates or optical isomers of K-351, and no method for their separation or resolution has been known.

The present inventors have studied the optical isomers of K-351 and their pharmacological activities, and have found that K-351 can be easily separated into two racemates, and the separated two racemates exhibit different pharmacological activities. The inventors have further discovered that by selectively administering one of the racemates to a patient according to his condition, the trouble of side effects can be reduced, and a therapeutic effect can be obtained efficiently.

Investigations of the present inventors have shown that separation of K-351 by, for example, recrystallization gives two kinds of crystals, i.e. a racemate having high crystallinity and a racemate having low crystallinity. A high-performance liquid chromatographic study of derivatives of these racemates has shown that the racemate having high crystallinity is a racemate (to be referred to as racemate K-351A in this invention) composed of an optical isomer (2'S),(3S) K-351 of the following formula (A-1) and an optical isomer (2'R),(3R) K-351 of the following formula (A-2), and that the racemate having low crystallinity is a racemate (to be referred to as racemate K-351B in this invention) composed of an optical isomer (2'R),(3S) K-351 of the following formula (B-1) and an optical isomer (2'S),(3R) K-351 of the following (B-2).

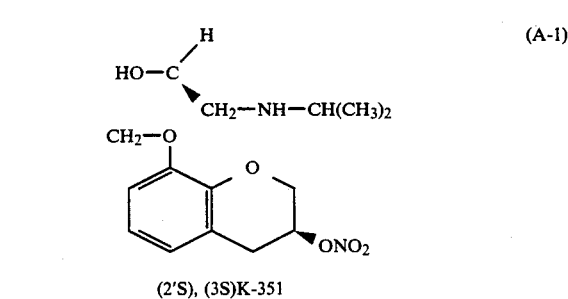

(2'S), (3S)K-351

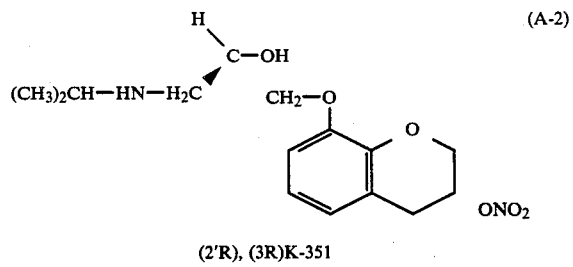

(2'R), (3R)K-351

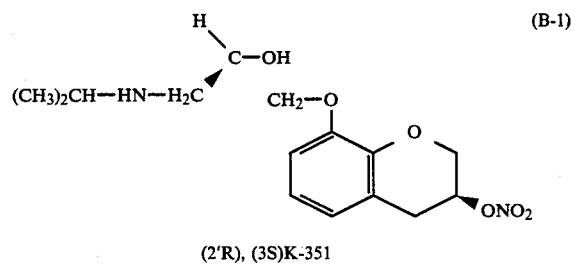

(2'R), (3S)K-351

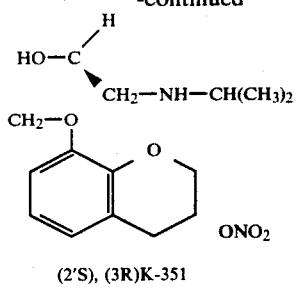

(2'S), (3R)K-351

The investigations of the present inventors have also shown that the racemate K-351A shows toxicity, vasodilating activity and hypotensive activity nearly equivalent to those of K-351 but its beta-blocking activity is about one-tenth of that of K-351, and that the racemate K-351B has toxicity, vasodilating activity and hypotensive activity nearly equivalent to those of K-351 but its beta-blocking activity is about 2 times as strong as that of K-351. The racemate K-351A has been found to be useful as drugs for cardiovascular diseases such as an agent for treating the hypertension of patients who have a tendency to cardiac failure, bradycardia, etc., an agent for treating angina pectoris with a spasm of the coronary artery, and an agent for treating mycoardial infarction. The racemate K-351B has been found to be useful as drugs for cardiovascular diseases such as a hypotensive agent and an antiarrhythmic agent.

It has been found therefore that by separating K-351 into these two racemates K-351A and K-351B and administering one of the racemates according to the condition of a patient, the patient can be treated efficiently with reduced manifestation of side-effects.

A method of obtaining one of the racemates K-351A and K-351B by separating K-351 into the two racemates and purifying them cannot give the desired one racemate in quantities, and is also disadvantageous in regard to industrial operations and cost. Further investigations of the inventors made in order to overcome this disadvantage have led to the finding of an industrially advantageous process for converting the racemate K-351A into the racemate K-351B or vice versa.

On the basis of the aforesaid findings, the present inventors disclosed the aforesaid two racemates K-351A and K-351B, processes for converting them and pharmaceutical compositions comprising them in Japanese Patent Application No. 36178/1984 (corresponding to European Patent Application No. 85301348.0).

On further investigations, the present inventors have succeeded in stereospecifically synthesizing the four optical isomers represented by the above formulae (A-1), (A-2), (B-1) and (B-2) which have previously been unable to be isolated.

The present inventors examined the pharmacological activities of these optical isomers, and found that the beta-blocking activity of R-R.K-351 of formula (A-2) is much weaker than that of K-351 but its vasodilating activity is equivalent to, or higher than, the vasodilating activity of K-351, and that S-R.K-351 of formula (B-2) shows the strongest beta-blocking and vasodilating activities among the aforesaid optical isomers. Investigations of the present inventors have shown that R-R.K-351 of formula (A-2) has beta-blocking activity about one-tenth of that of K-351, vasodilating activity about 1 to 1.5 times as high as that of K-351 and nearly equivalent hypotensive activity to K-351. Accordingly, R-R.K-351 has been found to be useful as a therapeutic agent for the hypertension of a patient having a tendency to cardiac failure, bradycardia, etc. and a therapeutic agent for angina pectoris with a spasm of the coronary artery.

The investigations of the present inventors have also shown that S-R.K-351 of formula (B-2) has beta-blocking activity about 3 to 8 times as high as that of K-351, direct vaso-relaxing activity about 1.2 times as high as that of K-351, alpha-blocking activity about two times as high as that of K-351, and hypotensive activity about 1.5 times as high as that of K-351. Accordingly, S-R.K-351 has been found to be useful as a hypotensive agent having strong beta-blocking activity and vasodilating activity.

It is an object of this invention to provide processes for producing novel optical isomers, R-R.K-351 and S-R.K-351 and acid addition salts thereof.

Another object of this invention is to provide the aforesaid novel optical isomers and the acid addition salts thereof.

Still another object of this invention is to provide a pharmaceutical composition comprising such a novel optical isomer or a pharmaceutically acceptable acid addition salt thereof.

The above and other objects and advantages of this invention will become apparent from the following description.

According to this invention, the optical isomers R-R.K-351 of formual (A-2) and S-R.K-351 of formula (B-2) can be easily produced by the following processe (a) or (b). The acid addition salts of such isomers can be easily produced by contacting the resulting R-R.K-351 and S-R.K-351 in the form of a free base with acids.

(a) A process which comprises reacting (3R)-3,4-dihydro-3-nitroxy-2H-1-benzopyran-8-ol of the following formula (II)

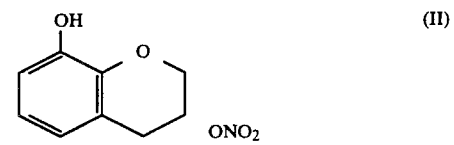

with a (2R)-epoxy compound represented by the following formula (IIIa)

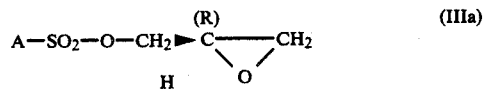

wherein A represents an alkyl, aralkyl or aryl group which may have a substituent, and thereafter contacting the resulting (2'R),(3R)-3,4-dihydro-8-(2',3'-epoxy)-propoxy-3-nitroxy-2H-1-benzopyran of the following formula (IVa)

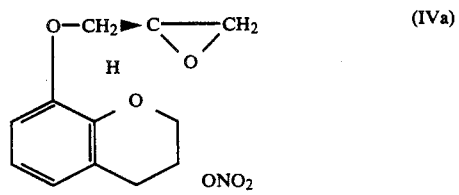

with isopropylamine to form (2'R),(3R)-3,4-dihydro-8-(2'-hydroxy-3'-isopropylamino)propoxy-3-nitroxy-2H-1-benzopyran of formula (A-2).

(b) A process which comprises reacting (3R)-3,4-dihydro-3-nitroxy-2H-1-benzopyran-8-ol of formula (II) with a (2S)-epoxy compound represented by the following formula (IIIb)

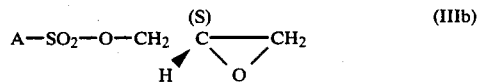

wherein A is as defined above, and thereafter contacting the resulting (2'S),(3R)-3,4-dihydro-8-(2',3'-epoxy)-propoxy-3-nitroxy-2H-1-benzopyran represented by the following formula (IVb)

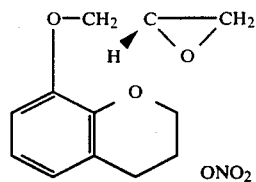

with isopropylamine to form (2'S),(3R)-3,4-dihydro-8-(2'-hydroxy-3'-isopropylamino)propoxy-3-nitroxy-2H-1-benzopyran of formula (B-2).

The starting compound of formual (II) can be easily produced from 3,4-dihydro-3-nitroxy-2H-1-benzopyran-8-ol of formula (I) given below. The above embodiments of production can be schematically shown as follows

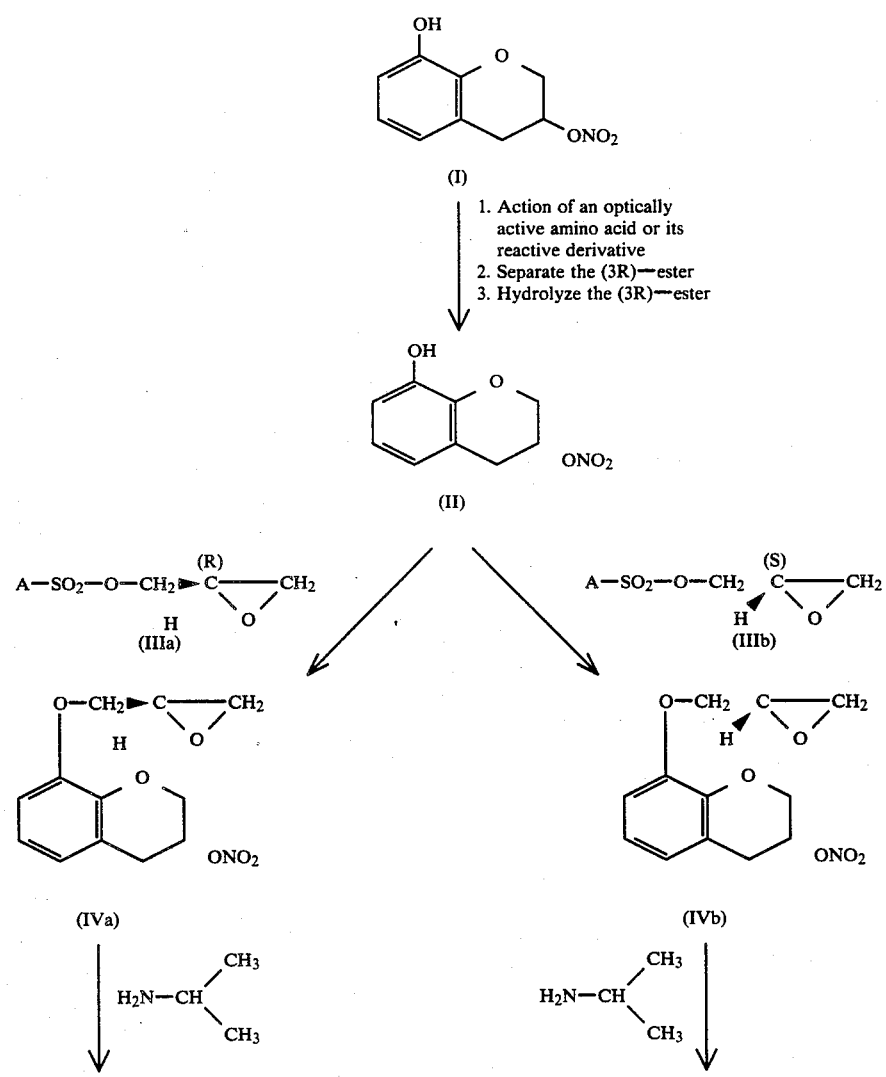

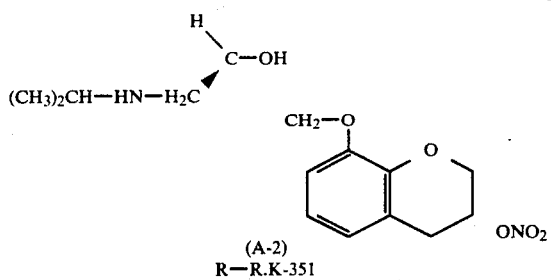
(A-2)
R—R.K-351

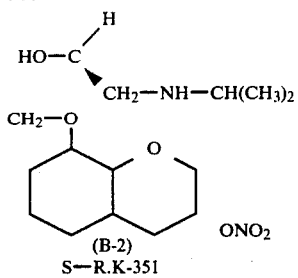
(B-2)
S—R.K-351

The synthesis of the optical isomers of this invention by the above embodiments will be described below in detail step by step.

(1) An optically active amino acid or its reactive derivative is caused to act on the 3,4-dihydro-3-nitroxy-2H-1-benzopyran to form an ester. The (3R) ester is separated and hydrolyzed to give (3R)-3,4-dihydro-3-nitroxy-2H-1-benzopyran (II).

The known compound of formula (I) can be obtained, for example, by protecting the 8-position hydroxyl group of 3,4-dihydro-3,8-dihydroxy-2H-1-benzopyran, esterifying the hydroxyl group at the 3-position with nitric acid, and splitting off the protective group for the 8-position hydroxyl group (see Japanese Laid-Open Patent Publication No. 167981/1982).

The optically active amino acid used in the formation of the ester may, for example, be L-phenylalanine and L-alanine. Preferably, the amino group of such amino acids is protected. Protective groups for the amino group may be suitably selected from those which are usually employed in the field of peptide synthesis. Examples include acyl groups such as acetyl, propionyl, benzoyl and p-niotrobenzoyl groups, sulfonyl groups such as mesyl, benzenesulfonyl and tosyl groups, alkyloxycarbonyl groups, cycloalkyloxycarbonyl groups, aralkyloxycarbonyl groups, and aryloxycarbonyl groups.

The above esterification reaction may also be carried out by the action of an optically active free amino acid on the compound of formula (I) in the presence of a dehydrating agent or condensing agent, or by the action of a reactive derivative of the optically active amino acid on the compound (I). An example of the dehydrating agent used in this reaction is N,N'-dicyclohexylcarbodiimide, and examples of the condensing agent are chloroformate esters, and phosphite esters. Examples of the reactive derivatives of the amino acid are acid chlorides, azides, acid anhydrides, mixed acid anhydrides, and active esters. Specific examples of the known active esters are phenyl esters, cyanomethyl esters, N-hydroxysuccinimide esters and N-hydroxyphthalimide esters which are known in the synthesis of peptides.

The ester-forming reaction described above can be carried out, for example, by reacting the compound of formula (I), the optically active amino acid and the dehydrating or condensing agent and a reactive derivative of the optically active amino acid in a solvent in the presence or absence of a base at a temperature of about 0° to 100° C. for about 1 to 30 hours. Examples of the solvent used in this reaction include halogenated hydrocarbons such as chloroform and methylene chloride, hydrocarbons such as n-hexane, benzene and toluene, and ethers such as diethyl ether, dioxane and tetrahydrofuran. The base is, for example, an amine such as triethylamine, pyridine or dimethylaminopyridine.

The (3R) ester may be separated from the resulting ester by utilizing, for example, recrystallization or chromatographic techniques. The recrystallization technique is particularly preferred. For example, recrystallization of an ester formed by using L-phenylalanine having the protected amino group gives the desired (3R) ester in the first place. Examples of suitable solvents used in the recrystallization technique include ethers such as diethyl ether, dioxane and tetrahydrofuran, hydrocarbons such as chloroform, methylene chloride, n-hexane, benzene, toluene and xylene, alcohols such as methanol, ethanol and propanol, and water. These solvents may be used singly or in combination.

Hydrolysis of the resulting optically active (3R) ester can give the (3R) 8-hydroxy compound (II). The hydrolysis can be carrid out by using acids or alkalies, but alkaline hydrolysis is preferred. Examples of the alkali used are alkali hydroxides such as sodium hydroxide and potassium hydroxide. The hydrolysis reaction can be carried out for several minutes to about 20 hours at a temperature of about 0° to about 100° C. in the aforesaid solvent.

(2) Action of the optically active (2R) epoxy compound of formula (IIIa) on the (3R) compound (II) obtained in (1) above gives (2'R),(3R)-3,4-dihydro-8-(2',3'-epoxy)-propoxy-3-nitroxy-2H-1-benzopyran (IVa).

The alkyl group as the substituent A of the epoxy compound (IIIa) is preferably a linear or branched alkyl group having 1 to 6 carbon atoms. Preferred aralkyl groups as substituent A are aralkyl groups having 7 or 8 carbon atoms such as benzyl and phenethyl groups. Preferred aryl groups as substituent A are aryl groups having 6 to 10 carbon atoms such as phenyl and naphthyl groups. These groups may be substituted by a halogen atom, a lower alkyl group (when A is an aralkyl or aryl group), a hydroxyl group, an alkoxy group, a nitro group, etc.

Preferably, the reaction is carried out in the presence of a base in a solvent. The solvent may be the same hydrocarbons, halogenated hydrocarbons and ethers as exemplified hereinabove for the reaction of the compound of formula (I) with the optically active amino acid or its reactive derivative. The reaction temperature can be properly selected, and is preferably −30° to about 150° C., and the reaction time is, for example, several minutes to about 10 hours.

(3) The desired R-R.K-351 can be obtained by contacting the (2'R),(3R)-epoxy compound (IVa) obtained in (2) above with isopropylamine. The contacting can be effected by reacting the compound (IVa) with isopropylamine in the presence or absence of the same solvent as exemplified hereinabove at a temperature of about 0° to about 150° C. for a period of several minutes to about 5 hours. Separation and purification of the resulting R-R.K-351 can be carried out in a customary manner.

(4) By the action of the optically active (2S) epoxy compound of formula (IIIb) on the (3R) compound in the same way as in (2) above, (2'S),(3R)-3,4-dihydro-8-(2',3'-epoxy)propoxy-3-nitroxy-2H-1-benzopyran (IVb) can be obtained. Action of isopropylamine on the (2'S),(3R)-epoxy compound (IVb) gives S-R.K-351. These reactions can be carried out under the same conditions as described above with regard to the production of R-R.K-351.

The R-R.K-351 and S-R.K-351 and pharmaceutically acceptable acid addition salts thereof have vasodilating activity and beta-blocking activity, and are useful as therapeutic agents for cardiovascular diseases.

Thus, the optical isomers of this invention, R-R.K-351 and S-R.K-351, may be used as agents for treating cardiovascular diseases in the form of free bases or pharmaceutically acceptable acid addition salts such as salts with hydrochloric acid, sulfuric acid, nitric acid, hydrobromic acid, acetic acid, lactic acid, oxalic acid, maleic acid and p-toluenesulfonic acid.

According to this invention, there is also provided a pharmaceutical composition comprising (1) an amount, effective for the treatment of cardiovascular diseases, of an optical isomer selected from the group consisting of (2'R),(3R)-3,4-dihydro-8-(2'-hydroxy-3'-isopropylamino)propoxy-3-nitroxy-2H-1-benzopyran represented by the following formula (A-2), (2'S),(3R)-3,4-dihydro-8-(2'-hydroxy-3'-isopropylamino)propoxy-3-nitroxy-2H-1-benzopyran represented by the following formula (B-2)

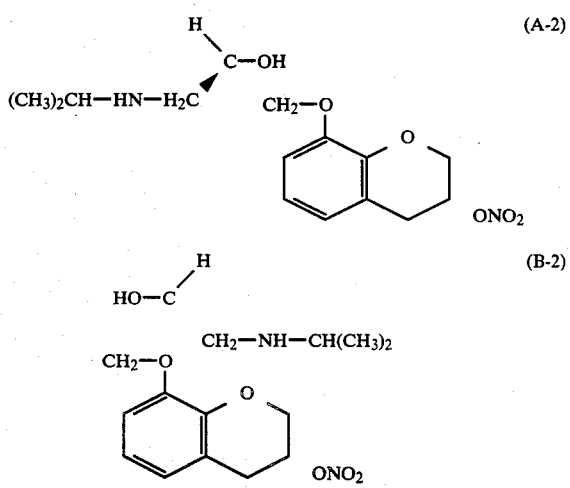

and pharmaceutically acceptable acid addition salts of these isomers, and (2) a pharmaceutically acceptable diluent or carrier.

The amount of the optical isomer or its acid addition salt in the pharmaceutical composition is, for example, about 0.01 to about 99% by weight based on the total weight of the pharmaceutical composition.

Liquid or solid carriers or diluents may be used in formulating the pharmaceutical composition of this invention. They may include excipients, binders, lubricants, emulsifiers, etc. known in pharmaceutical production. Examples of these carriers or diluents include starches such as potato starch, wheat starch, corn starch and rice starch; sugars such as lactose, sucrose, glucose, mannitol and sorbitol; celluloses such as crystalline cellulose, calcium carboxymethyl cellulose and hydroxypropyl cellulose of a low degree of substitution; inorganic substances such as potassium phosphate, calcium sulfate, calcium carbonate and talc; binder compounds such as gelatin, gum arabic, methyl cellulose, sodium carboxymethyl cellulose, polyvinyl pyrrolidone and hydroxypropyl cellulose; polyhydric alcohol ester-type nonionic surfactants such as fatty acid monoglycerides, sorbitan fatty acid esters, sucrose and polyglycerol fatty acid esters; and polyoxyethylene-type nonionic surfactants.

The pharmaceutical compositions may be in any dosage forms known in the art of formulating pharmaceuticals, such as suppositories, powders, granules, tablets, sublingual tablets, liquid preparations, injectable preparations and suspensions.

The pharmaceutical compositions of this invention may be administered through any of peroral and parenteral routes, such as an intravenous, sublingual or intrarectal route. For long-term administration, the oral route is preferred.

The dose may be changed as desired. For example, the R-R.K-351, S-R.K-351, or a pharmaceutically acceptable acid addition salt thereof may be administered in a dose of about 1 to about 100 mg/body/day, preferably about 5 to about 50 mg/body/day. The compounds of this invention have low toxicity.

Some examples are given below for testing the pharmacological efficacy of the compounds in accordance with this invention.

EXPERIMENTAL EXAMPLE 1 beta-Blocking activity

The compounds indicated in Table 1 were tested for their antagonistic action on isoproterenol, i.e. their beta-blocking action, using isolated atrium and trachea of guinea pigs. The results are shown in Table 1.

In the table, $pA_2$ shows the reciprocal logarithm of the molar concentration of each test compound required to shift the dose-response curve of isoproterenol parallel toward a higher dose side by 2 times.

The parenthesized figures show efficacy ratios based on K-351.

The results demonstrate that the beta-blocking activity of R-R.K-351 is about one-tenth of that of K-351, and the beta-blocking activity of S-R.K-351 is about 3 to 8 times as strong as that of K-351.

TABLE 1

| Compound tested | $pA_2$ | | |
| --- | --- | --- | --- |
| | Atrium | | |
| | Heart rate | Contracting force | Trachea |
| K-351 | 9.1 | 8.7 | 8.49 |
| | (1.0) | (1.0) | (1.0) |
| S-R.K-351 (invention) | 9.6 | 9.6 | 9.18 |
| | (3.2) | (7.9) | (4.9) |
| S-S.K-351 (formula A-1) | 8.0 | 8.2 | 7.60 |
| | (0.1) | (0.3) | (0.13) |
| R-R.K-351 (invention) | 7.6 | 7.7 | 7.39 |
| | (0.03) | (0.1) | (0.08) |
| R-S.K-351 (formula B-1) | 5.8 | 5.5 | 5.84 |
| | (0.0005) | (0.0005) | (0.002) |

EXPERIMENTAL EXAMPLE 2

Vasodilating activity

The compounds indicated in Table 2 were tested for their antagonistic action on potassium contracture (direct vaso-relaxing activity) and their antagonistic action on the contractile activity of norepinephrine (NE) (alpha-blocking activity) using the isolated superior mesenteric artery of dogs. The results are shown in Table 2.

In the table $pD_2$ represents the reciprocal logarithm of the molar concentration of each test compound required to inhibit the maximum reaction of potassium (25 m $MK^+$) by an extent of 50%; and $pA_2$ represents the reciprocal logarithm of the molar concentration of each test compound required to shift the dose-response curve of norepinephrine parallel toward a high dose side by 2 times.

The parenthesized figures have the same meanings as indicated above with reference to Table 1.

The above results demonstrate that the vasodilating activity of R-R.K-351 is nearly equivalent to that of K-351, and the vasodilating activity of S-R.K-351 is about 1.1 to 2 times as high as that of K-351.

TABLE 2

| Compound tested | $K^+$ contracture [$pD_2$] | NE contraction [$pA_2$] |
| --- | --- | --- |
| K-351 | 6.17 | 6.81 |
|  | (1.00) | (1.00) |
| S-R.K-351 | 6.24 | 7.12 |
| (invention) | (1.17) | (2.04) |
| R-R.K-351 | 6.35 | 6.75 |
| (invention) | (1.51) | (0.87) |
| S-S.K-351 | 4.69 | 5.65 |
| (formula A-1) | (0.03) | (0.07) |
| R-S.K-351 | 4.77 | 5.51 |
| (formula B-1) | (0.04) | (0.05) |

EXPERIMENTAL EXAMPLE 3

Hypotensive activity

The compounds indicated in Table 3 were intravenously administered in a dose of 100 γ/kg to anesthetized dogs, and changes in average blood pressure and heart rate were determined. The results are shown in Table 3. Each of the test compounds was used in the form of a solution in physiological saline together with an equimolar amount of hydrochloric acid which contained the test compound in a concentration of 1 mg/ml.

The results demonstrate that the hypotensive activity of R-R.K-351 is nearly equivalent to that of K-351, and the hypotensive activity of S-R.K-351 is about 1.5 times as high as that of K-351.

REFERENTIAL EXAMPLE 1

Production of (2R)-3-(o-nitrobenzenesulfonyloxy)-1,2-epoxypropane (A) 8.6 g of (R)-glycerol acetonide [bp.: 88°–106° C. (18 mmHg); specific rotation: $[\alpha]_D^{25} - 12.10°$ (c 5.64, methanol)] was dissolved in 70 ml of chloroform, and 10.0 g of triethylamine was added. With stirring and ice cooling, a solution of 13.8 g of tosyl chloride in 30 ml of chloroform was added dropwise, and the mixture was stirred overnight. The reaction mixture was washed with an aqueous solution of potassium hydrogen carbonate and water, and the solvent was evaporated. The residue (18.7 g) was dissolved in 75 ml of acetone, and 225 ml of 1N hydrochloric acid was added. The mixture was stirred at 80° C. for 30 minutes. The reaction mixture was concentrated and extracted with 450 ml of ethyl acetate. The extract was washed with water, and the solvent was evaporated. The residue was purified by silica gel column chromatography [solvent: chloroform-methanol (40:1)] to give 10.86 g (yield 67.8%) of (S)-3-tosyloxy-1,2-propanediol as colorless needles having a melting point of 57° to 60° C.

Specific rotation: $[\alpha]_D^{25} + 9.66°$ (c 7.35, $CH_3OH$).

$^1H$-NMR: $\delta CDCl_3$, ppm; 2.40 (3H, S, $CH_3$),

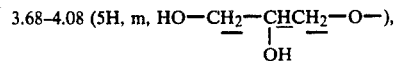

3.68–4.08 (5H, m, HO—$CH_2$—$CHCH_2$—O—),
                               |
                              OH 7.25 (2H, d, J=7.5 Hz, aromatic H), 7.70 (2H, d, J=7.5 Hz, aromatic H).

(B) 14.90 g of the diol compound obtained in (A) above was dissolved in 150 ml of tetrahydrofuran, and with ice cooling, 6.49 g of sodium methoxide was added. The mixture was stirred for 2 hours. To the reaction mixture was added 27.8 ml of triethylamine, and a solution of 22.2 g of o-nitrobenzenesulfonyl chloride in 50 ml of tetrahydrofuran was added dropwise. The mixture was stirred overnight. The reaction mixture was filtered, and the filtrate was concentrated. The residue was purified by silica gel column chromatography [solvent: benzene-chloroform (2:1)] to give 7.31 g (yield 46.6%) of the desired compound as a pale yellow viscous oil.

Specific rotation: $[\alpha]_D^{25} + 2.8°$ (c 15.2, $CHCl_3$).

$^1H$-NMR: $\delta CDCl_3$, ppm;

TABLE 3

| Test compound | | Time elapsed (minutes) | | | | | |
| --- | --- | --- | --- | --- | --- | --- | --- |
| | | 1 | 5 | 10 | 15 | 30 | 60 |
| K-351 | Average blood pressure (mm/Hg) | −19 | −19 | −17 | −16 | −12 | −8 |
| | Heart rate (beats/min.) | −21 | −37 | −40 | −42 | −44 | −42 |
| S-R.K-351 (invention) | Average blood pressure (mm/Hg) | −33 | −23 | −21 | −19 | −18 | −16 |
| | Heart rate (beats/min.) | −24 | −36 | −40 | −40 | −40 | −40 |
| S-S.K-351 (formula A-1) | Average blood pressure (mmHg) | −12 | −6 | −4 | −4 | −4 | −2 |
| | Heart rate (beats/min.) | −32 | −34 | −34 | −34 | −32 | −30 |
| R-R.K-351 (invention) | Average blood pressure (mmHg) | −26 | −13 | −12 | −10 | −6 | −2 |
| | Heart rate (beats/min.) | −5 | −9 | −10 | −10 | −11 | −13 |
| R-S.K-351 (formula B-1) | Average blood pressure (mmHg) | −1 | −1 | −1 | −1 | −1 | |
| | Heart rate (beats/min.) | −2 | −2 | −1 | −1 | 0 | |

2.60-2.90 (2H, m, —C<u>H</u>——CH₂<u></u>), 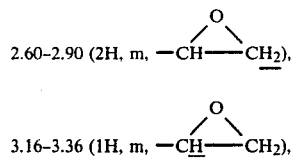

3.16-3.36 (1H, m, —C<u>H</u>——CH₂), 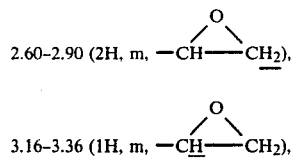

4.00-4.66 (2H, m, —O—CH₂—S—), 7.62-8.16 (4H, m, aromatic H).

IR: $\nu_{max}^{Film}$, cm⁻¹;

3000 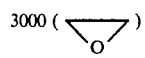

1365 and 1180 (SO₂)

Elemental analysis for C₉H₉NO₆S:

|  | C | H | N |
|---|---|---|---|
| Calculated (%) | 41.70 | 3.50 | 5.40 |
| Found (%) | 41.66 | 3.52 | 5.18 |

REFERENTIAL EXAMPLE 2

Production of (2S)-3-(o-nitrobenzenesulfonyloxy)-1,2-epoxypropane 24.4 g of (R)-3-tosyloxy-1,2-propanediol [mp.: 60°–62° C.; specific rotation: $[\alpha]_D^{24}$ −9.25° (c 2.12, methanol)] was dissolved in a mixture of 30 ml of methanol and 15 ml of ether. With ice cooling and stirring, 6.5 g of sodium methoxide was added in four portions at intervals of one hour. The insoluble materials were then removed by filtration from the reaction mixture, and the solvent as evaporated at below 30° C. to give 8.4 g of crude (R)-glycidol. The crude product (8.4 g) was dissolved in 120 ml of tetrahydrofuran and 11.1 g of triethylamine was added. Then, 24.2 g of o-nitrobenzenesulfonyl chloride was added with cooling and stirring, and the mixture was stirred for 2 hours. The insoluble materials were removed from the reaction mixture by filtration, and the solvent was evaporated. The residue was purified by silica gel column chromatography [solvent: benzene-chloroform (2:3)] to give 15.45 g (yield 60.1%) of the desired product.

Specific rotation: $[\alpha]_D^{25}$ −2.8° (c 10.0, CHCl₃).

¹H-NMR: δCDCl₃, ppm;

2.60-2.92 (2H, m, —C<u>H</u>——CH₂<u></u>), 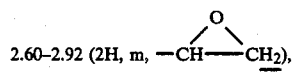

3.16-3.36 (1H, m, —C<u>H</u>——CH₂), 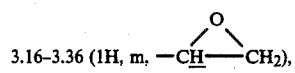

4.00-4.66 (2H, m, —CH₂—O—S), 7.60-8.16 (4H, m, aromatic H).

IR: $\nu_{max}^{Film}$, cm⁻¹;

3010 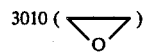

1370 and 1190 (SO₂).

Elemental analysis for C₉H₉NO₆S:

|  | C | H | N |
|---|---|---|---|
| Calculated (%) | 41.70 | 3.50 | 5.40 |
| Found (%) | 41.76 | 3.51 | 5.29 |

EXAMPLE 1

(A) Production of (3R)-3,4-dihydro-8-(N-mesyl-L-phenylalanyloxy)-3-nitroxy-2H-1-benzopyran 31.8 g of 3,4-dihydro-8-hydroxy-3-nitroxy-2H-1-benzopyran was dissolved in 500 ml of methylene chloride, and 36.6 g of N-mesyl-L-phenylalanine and 3.7 g of 4-dimethylaminopyridine were added. With stirring at room temperature, a solution of 40 g of dicyclohexylcarbodiimide in 130 ml of methylene chloride was added, and the mixture was stirred overnight at room temperature. The precipitate was removed from the reaction mixture by filtration. The filtrate was concentrated, and the residue was dissolved in ethyl acetate and washed successively with 5% hydrochloric acid, a 5% aqueous solution of sodium hydroxide and water. The solvent was then evaporated. The residue was dissolved in tetrahydrofuran. The insoluble materials were removed by filtration. Hexane was added, and the solution was left to stand. The precipitated crystals were collected by filtration, and recrystallized from acetone to give 12.8 g (yield 19.4%) of the desired product as colorless prisms having a melting point of 191° to 195° C. (decomp.).

Specific rotation: $[\alpha]_D^{25}$ −17.2° (c 3, THF).

¹H-NMR: δCDCl₃, ppm; 2.74 (3H, s, —CH₃), 3.08-3.50 (4H, m, C₄—H and —CH₂— 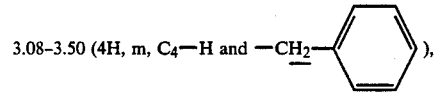 ), 4.24-4.36 (2H, m, C₂—H), 4.60-4.80 (1H, m, —C<u>H</u>NH), 4.92 (1H, d, J=9 Hz, —NH), 5.36-5.56 (1H, m, C₃—H), 6.80-7.10 (3H, m, aromatic H), 7.32 (5H, s, aromatic H).

IR: $\nu_{max}^{KBR}$, cm⁻¹; 3240 (NH), 1778 (COO), 1635 and 1272 (ONO₂), 1325 and 1150 (SO₂NH).

Mass spectrum: m/e; 436 (M+)

Elemental analysis for C₁₉H₂₀N₂O₈S:

|  | C | H | N |
|---|---|---|---|
| Calculated (%) | 52.29 | 4.62 | 6.42 |
| Found (%) | 52.51 | 4.74 | 6.27 |

(B) Production of (3R)-3,4-dihydro-3-nitroxy-2H-1-benzopyran-8-ol 21.6 g of the ester obtained in (A) was dissolved in 200 ml of tetrahydrofuran, and at room temperature, 100 ml of methanol and then 40 ml of a 10% aqueous solution of sodium hydroxide were added. The mixture was stirred for 1 hour. The reaction mixture was adjusted to a pH of about 4 with cold hydrochloric acid, and concentrated. To the residue were added 300 ml of chloroform and dilute hydrochloric acid. The aqueous layer was adjusted to pH 2, and the chloroform layer was separated. The chloroform layer was washed with an aqueous solution of sodium hydrogen carbonate and also with water, and the solvent was evaporated. Recrystallization of the residue from ethyl acetate-hexane gave 9.2 g (yield 38.0%) of the desired product as colorless prisms having a melting point of 129.0° to 130.5° C.

Specific rotation: $[\alpha]_D^{25} + 40.8°$ (c 3, CHCl$_3$).

$^1$H-NMR: $\delta$CDCl$_3$, ppm; 2.84–3.42 (2H, m, C$_4$—H), 4.12–4.52 (2H, m, C$_2$—H), 5.32–5.50 (1H, m, C$_3$—H), 5.44 (1H, s, OH), 6.48–6.90 (3H, m, aromatic H).

IR: $\nu_{max}^{KBR}$, cm$^{-1}$; 3330 (OH), 1620 and 1290 (ONO$_2$).

Elemental analysis for C$_9$H$_9$NO$_5$:

|  | C | H | N |
|---|---|---|---|
| Calculated (%) | 51.19 | 4.30 | 6.63 |
| Found (%) | 51.13 | 4.30 | 6.56 |

(C) Production of (2′R),(3R)-3,4-dihydro-8-(2′,3′-epoxy)propoxy-3-nitroxy-2H-1-benzopyran 3.75 g of the (3R)-8-hydroxy compound obtained in (B) was dissolved in 30 ml of anhydrous tetrahydrofuran, and with ice cooling, a suspension of 0.85 g of 50% sodium hydride in 9 ml of tetrahydrofuran was added. The mixture was stirred for 15 minutes. A solution of 4.6 g of the (2R)-3-(o-nitrobenzenesulfonyloxy)-1,2-epoxypropane obtained in Referential Example 1 in 25 ml of tetrahydrofuran was added, and the mixture was stirred at a bath temperature of 70° to 75° C. for 1.5 hours. The precipitate was removed from the reaction mixture by filtration, and the solvent was evaporated. The residue was dissolved in 50 ml of chloroform, and washed with a 5% aqueous solution of sodium hydroxide and then with water. The solvent was evaporated. Recrystallization of the residue from acetone-methanol methanol gave 3.89 g (yield 82.0%) of the desired product as colorless needles having a melting point of 141.0° to 142.5° C.

Specific rotation: $[\alpha]_D^{25} + 34.0°$ (c 2, CHCl$_3$);
$^1$H-NMR: $\delta$CDCl$_3$, ppm;

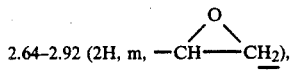
2.64–2.92 (2H, m, —CH——CH$_2$),

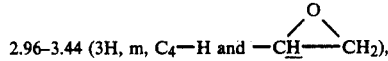
2.96–3.44 (3H, m, C$_4$—H and —CH——CH$_2$), 3.84–4.52 (4H, m, C$_2$—H and —OCH$_2$CH<), 5.26–5.48 (1H, m, C$_3$—H), 6.52–6.88 (3H, m, aromatic H).

IR: $\nu_{max}^{KBR}$, cm$^{-1}$; 1620 and 1280 (ONO$_2$).

Elemental analysis for C$_{12}$H$_{13}$NO$_6$:

|  | C | H | N |
|---|---|---|---|
| Calculated (%) | 53.93 | 4.90 | 5.24 |
| Found (%) | 53.70 | 4.82 | 5.13 |

(D) Production of (2′R),(3R)-3,4-dihydro-8-(2′-hydroxy-3′-isopropylamino)propoxy-3-nitroxy-2H-1-benzopyran (R-R.K-351)

40 ml of isopropylamine and 80 ml of ethanol were mixed, and 3.9 g of the (2′S),(3R)-epoxy compound obtained in (C) above was added to the mixture. The mixture was stirred at a bath temperature of 70° C. for 1 hour. The solvent was evaporated from the reaction mixture. The residue was dissolved in chloroform and extracted with an aqueous solution of acetic acid. The extract was washed with benzene, made alkaline with an aqueous solution of sodium hydroxide, and extracted with chloroform. The extract was washed with water, and the solvent was evaporated. The residue was purified by alumina column chromatography (solvent: chloroform), and then recrystallized from benzene-hexane to give 4.08 g (yield 85.7%) of the desired product as colorless needles having a melting point of 144.0° to 144.5° C.

Specific rotation: $[\alpha]_D^{25} + 15.5°$ (c 2, CHCl$_3$);

$^1$H-NMR: $\delta$CDCl$_3$, ppm 1.07 (6H, d, J=6 Hz, CH$_3$), 2.20–3.44 (7H, m, C$_4$—H, —CH$_2$NHCH< and OH), 3.92–4.16 (3H, m, —OCH$_2$CH(OH)—), 4.16–4.54 (2H, m, C$_2$—H), 5.33–5.53 (1H, m, C$_3$—H), 6.58–6.92 (3H, m, aromatic H).

IR: $\nu_{max}^{KBR}$, cm$^{-1}$; 1620 and 1278 (ONO$_2$).

Elemental analysis for C$_{15}$H$_{22}$N$_2$O$_6$:

|  | C | H | N |
|---|---|---|---|
| Calculated (%) | 55.21 | 6.79 | 8.58 |
| Found (%) | 55.13 | 6.81 | 8.43 |

EXAMPLE 2

(A) Production of (2′S),(3R)-3,4-dihydro-8-(2′,3′-epoxy)propoxy-3-nitroxy-2H-1-benzopyran 3.75 g of the (3R)-8-hydroxy compound obtained in Example 1, (B) was dissolved in 30 ml of anhydrous tetrahydrofuran, and with ice cooling, a suspension of 0.85 g of 50% sodium hydride in 9 ml of tetrahydrofuran was added. The mixture was stirred for 15 minutes. To the reaction mixture was added a solution of 4.6 g of the (2S)-3-(o-nitrobenzenesulfonyloxy)-1,2-epoxypropane obtained in Referential Example 2 in 25 ml of tetrahydrofuran, and the mixture was stirred at a bath temperature of 70° to 75° C. for 1.5 hours. The precipitate was removed from the reaction mixture by filtration, and the solvent was evaporated. The residue was dissolved in 50 ml of chloroform, and washed with a 5% aqueous solution of sodium hydride and then with water. The solvent was evaporated. Recrystallization of the residue from acetone-methanol gave 4.3 g (yield 90.6%) of the desired product as colorless needles having a melting point of 131.5° to 132.0° C.

Specific rotation: $[\alpha]_D^{25} + 25.3°$ (c 2, CHCl$_3$).

$^1$H-NMR: $\delta$CDCl$_3$, ppm

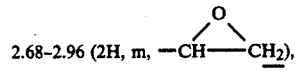
2.68–2.96 (2H, m, —CH——CH$_2$),

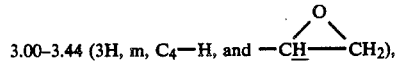
3.00–3.44 (3H, m, C$_4$—H, and —CH——CH$_2$), 3.92–4.52 (4H, m, C$_2$—H and —OCH$_2$CH<), 5.28–5.52 (1H, m, C$_3$—H), 6.57–6.92 (3H, m, aromatic H).

IR: $\nu_{max}^{KBR}$, cm$^{-1}$; 1620 and 1280 (ONO$_2$).

Elemental analysis for C$_{12}$H$_{13}$NO$_6$:

|  | C | H | N |
|---|---|---|---|
| Calculated (%) | 53.93 | 4.90 | 5.24 |

-continued

|           | C     | H    | N    |
|-----------|-------|------|------|
| Found (%) | 53.71 | 4.85 | 5.12 |

(B) Production of (2'S),(3R)-3,4-dihydro-8-(2'-hydroxy-3'-isopropylamino)propoxy-3-nitroxy-2H-1-benzopyran (S-R.K-351)

40 ml of isopropylamine and 80 ml of ethanol were mixed, and 3.9 g of the (2'S),(3R)-epoxy compound obtained in (A) above was added to the mixture. The mixture was stirred at a bath temperature of 70° C. for 1 hour. The solvent was evaporated from the reaction mixture. The residue was dissolved in chloroform and extracted with an aqueous solution of acetic acid. The extract was washed with benzene, made alkaline with an aqueous solution of sodium hydroxide, and extracted with chloroform. The extract was washed with water, and the solvent was evaporated. The residue was purified by alumina column chromatography (solvent: chlorofrom), and recrystallized from benzene-hexane to give 3.91 g (yield 82.1%) as colorless needles having a melting point of 107.5° to 108.5° C.

Specific rotation: $[\alpha]_D^{25} + 16.2°$ (c 2, CHCl$_3$).

$^1$H-NMR: $\delta$CDCl$_3$, ppm 1.07 (6H, d, J=6 Hz, CH$_3$), 2.20–3.44 (7H, m, C$_4$—H, —CH$_2$NH$\underline{C}$H< and OH),

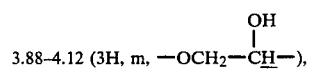
3.88–4.12 (3H, m, —OCH$_2$—C$\underline{H}$—), 4.12–4.52 (2H, m, C$_2$—H), 5.32–5.52 (1H, m, C$_3$—H), 6.56–6.92 (3H, m, aromatic H).

IR: $\nu_{max}^{KBR}$, cm$^{-1}$; 1620 and 1278 (ONO$_2$).

Elemental analysis for C$_{15}$H$_{22}$N$_2$O$_6$:

|                | C     | H    | N    |
|----------------|-------|------|------|
| Calculated (%) | 55.21 | 6.79 | 8.58 |
| Found (%)      | 55.19 | 6.76 | 8.53 |

FORMULATION EXAMPLE 1

| Tablets:                      |         |
|-------------------------------|---------|
| R-R.K-351                     | 6 parts |
| Crystalline cellulose         | 50 parts |
| Lactose                       | 34 parts |
| Carboxymethyl cellulose calcium | 9 parts |
| Magnesium stearate            | 1 part  |

The above ingredients were uniformly mixed and tableted into tablets each having a diameter of 5 mm and weighing 50 mg by a direct tableting method.

FORMULATION EXAMPLE 2

| Granules: | | |
|---|---|---|
| A | S-R.K-351 | 1 part |
|   | Crystalline cellulose | 25 parts |
|   | Lactose | 40 parts |
|   | Corn starch | 32 parts |
| B | Hydroxypropyl cellulose | 2 parts |
|   | Ethanol | 25 parts |

The ingredients in (A) were uniformly mixed and then kneaded with the solution (B). The mixture was granulated by an extrusion method, dried in vacuum at 50° C., and sieved to form granules.

FORMULATION EXAMPLE 3

| Capsules:             |          |
|-----------------------|----------|
| S-R.K-351             | 10 parts |
| Lactose               | 40 parts |
| Crystalline cellulose | 30 parts |
| Talc                  | 10 parts |

The above ingredients were uniformly mixed. 90 mg of the resulting mixture were filled in each of No. 5 lock capsules to form capsules.

What is claimed is:

1. An optical isomer selected from the group consisting of (2'R),(3R)-3,4-dihydro-8-(2'-hydroxy-3'-isopropylamino)propoxy-3-nitroxy-2H-1-benzopyran represented by the following formula (A-2), (2'S),(3R)-3,4-dihydro-8-(2'-hydroxy-3'-isopropylamino)propoxy-3-nitroxy-2H-1-benzopyran represented by the following formula (B-2)

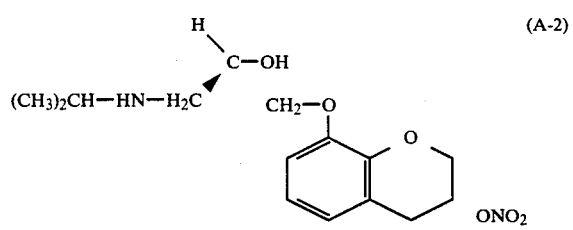

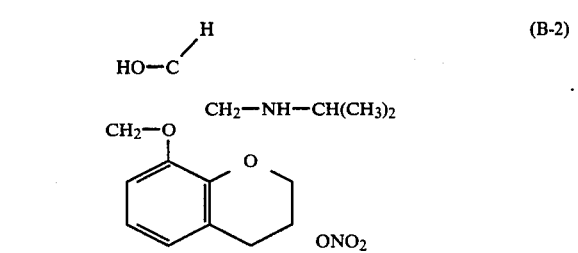

and pharmaceutically acceptable acid addition salts of these isomers.

2. A pharmaceutical composition comprising
(1) an amount, effective for the treatment of cardiovascular disseases, of an optical isomer selected from the group consisting of (2'R),(3R)-3,4-dihydro-8-(2'-hydroxy-3'-isopropylamino)propoxy-3-nitroxy-2H-1-benzopyran represented by the following formula (A-2), (2'S),(3R)-3,4-dihydro-8-(2'-hydroxy-3'-isopropylamino)-propoxy-3-nitroxy-2H-1-benzopyran represented by the following formula (B-2)

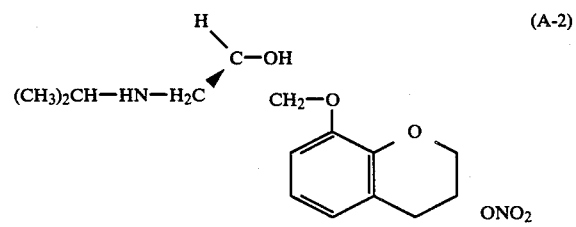

-continued
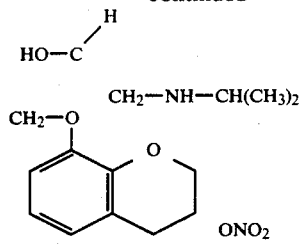
(B-2)
or a pharmaceutically acceptable acid addition salt of said isomer, and
(2) a pharmaceutically acceptable diluent or carrier.
3. The pharmaceutical composition of claim 2 wherein the amount of the optical isomer or its acid addition salt is about 0.01 to about 99% by weight based on the total weight of the pharmaceutical composition.
* * * * *

UNITED STATES PATENT AND TRADEMARK OFFICE
CERTIFICATE OF CORRECTION

PATENT NO. : 4,678,803
DATED : 07/07/87
INVENTOR(S) : Masami SHIRATSUCHI; Kiyoshi KAWAMURA; Toshihiro AKASHI; Hiroshi ISHIHAMA; Yasumi UCHIDA It is certified that error appears in the above-identified patent and that said Letters Patent is hereby corrected as shown below:

Rewrite formula (A-2), all occurrences as it appears in the patent in cols. 1, 2, 7, 9 and 18, as follows:

--
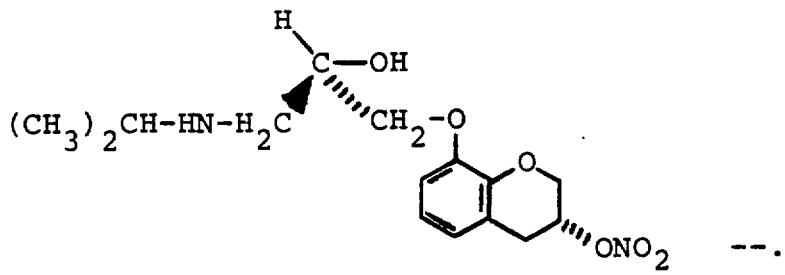
--.

Rewrite formula (B-2), all occurrences as it appears in the patent in cols. 1, 3, 8, 9, 18 and 19, as follows:

--
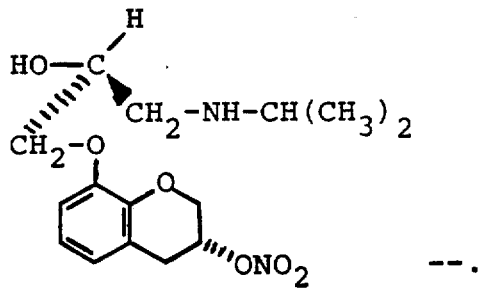
--.

UNITED STATES PATENT AND TRADEMARK OFFICE
CERTIFICATE OF CORRECTION

PATENT NO. : 4,678,803          Page 2 of 5
DATED : 07/07/87
INVENTOR(S) : Masami SHIRATSUCHI; Kiyoshi KAWAMURA; Toshihiro AKASHI; Hiroshi ISHIHAMA; Yasumi UCHIDA It is certified that error appears in the above-identified patent and that said Letters Patent is hereby corrected as shown below:

Rewrite formula (A-1), col. 2, as follows:

-- 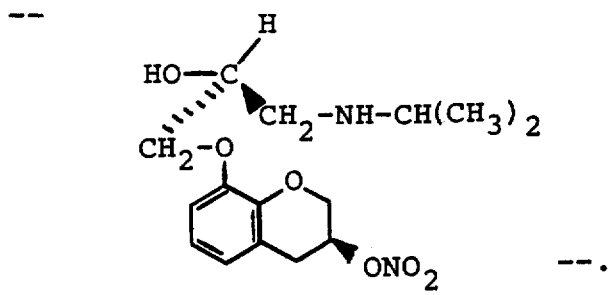 --.

Rewrite formula (B-1), col. 2, as follows:

-- 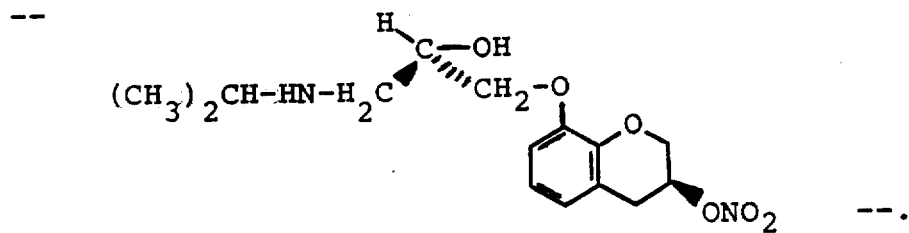 --.

UNITED STATES PATENT AND TRADEMARK OFFICE
CERTIFICATE OF CORRECTION

PATENT NO. : 4,678,803
DATED : 07/07/87
INVENTOR(S) : Masami SHIRATSUCHI; Kiyoshi KAWAMURA; Toshihiro AKASHI; Hiroshi ISHIHAMA; Yasumi UCHIDA It is certified that error appears in the above-identified patent and that said Letters Patent is hereby corrected as shown below:

Rewrite formula (II), col. 4, as follows:

-- 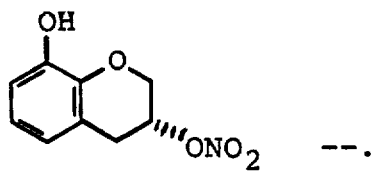 --.

Rewrite formula (IIIa), col. 4, as follows:

-- 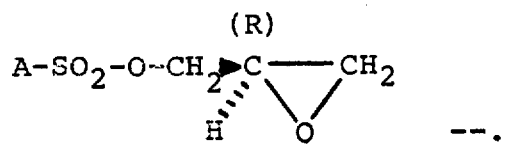 --.

Rewrite formula (IVa), col. 4, as follows:

-- 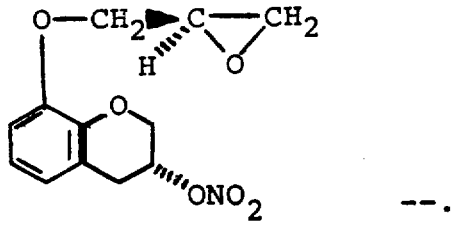 --.

UNITED STATES PATENT AND TRADEMARK OFFICE
CERTIFICATE OF CORRECTION

PATENT NO. : 4,678,803
DATED : 07/07/87
INVENTOR(S) : Masami SHIRATSUCHI; Kiyoshi KAWAMURA; Toshihiro AKASHI; Hiroshi ISHIHAMA; Yasumi UCHIDA It is certified that error appears in the above-identified patent and that said Letters Patent is hereby corrected as shown below:

Cols. 5 and 6, bottom of page, rewrite the reaction scheme so that the formulas read as follows:

--

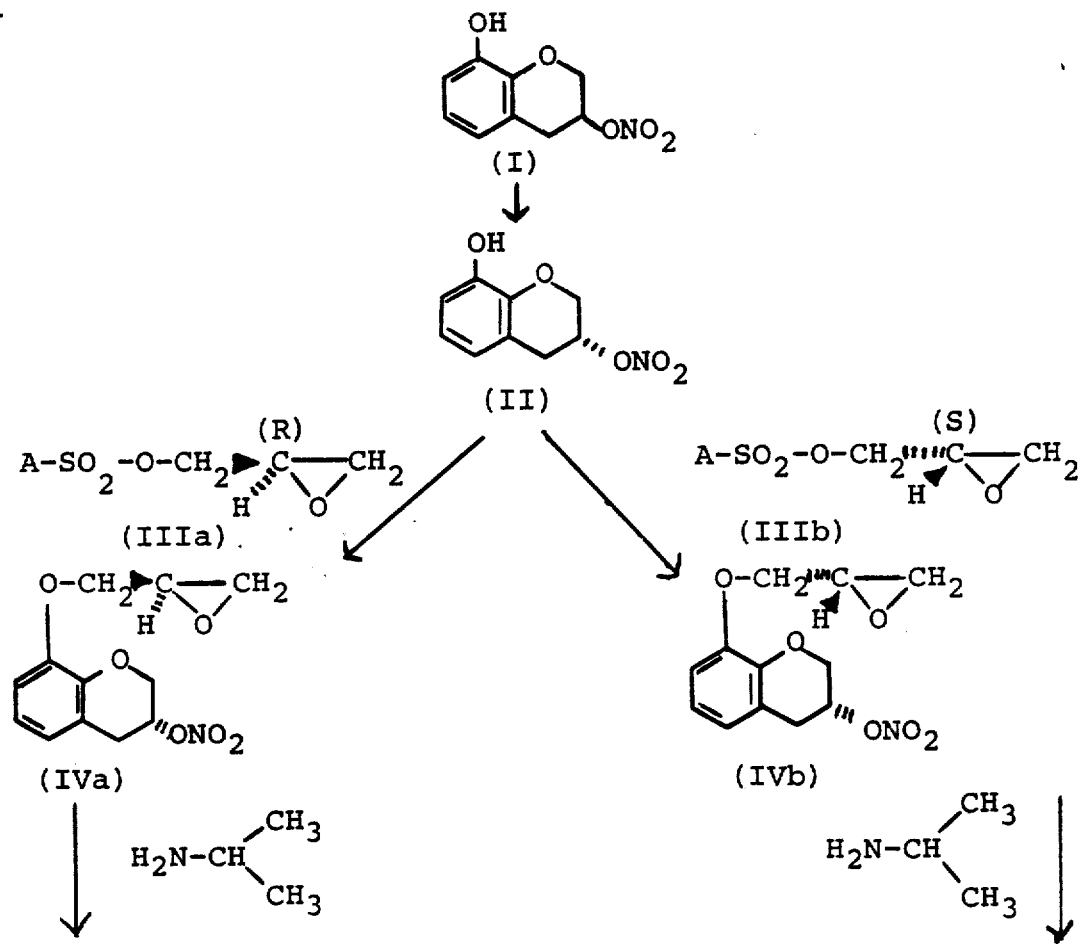

UNITED STATES PATENT AND TRADEMARK OFFICE
CERTIFICATE OF CORRECTION

PATENT NO. : 4,678,803

DATED : 07/07/87

INVENTOR(S) : Masami SHIRATSUCHI; Kiyoshi KAWAMURA; Toshihiro AKASHI; Hiroshi ISHIHAMA; Yasumi UCHIDA It is certified that error appears in the above-identified patent and that said Letters Patent is hereby corrected as shown below:

Rewrite formula (IIIb), col. 5, (top of page) as follows:

--  --.

Rewrite formula (IVb), col. 6 (top of page) as follows:

-- 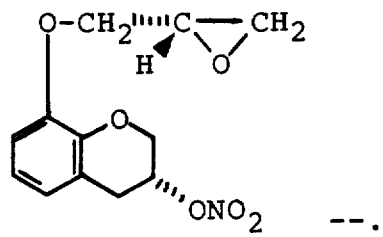 --.

Signed and Sealed this

Third Day of April, 1990

Attest:

HARRY F. MANBECK, JR.

Attesting Officer

Commissioner of Patents and Trademarks